US005698404A

United States Patent [19]
Strauss, III et al.

[11] Patent Number: 5,698,404
[45] Date of Patent: *Dec. 16, 1997

[54] METHOD OF PREDICTING FETAL MEMBRANE RUPTURE BASED ON PRO-MATRIX METALLOPROTEINASE-9 (PRO-MMP-9)

[75] Inventors: Jerome Frank Strauss, III, Wyndmoor, Pa.; Felipe Vadillo-Ortega, La Magdalena, Mexico

[73] Assignee: University of Pennsylvania, Philadelphia, Pa.

[*] Notice: The term of this patent shall not extend beyond the expiration date of Pat. No. 5,641,630.

[21] Appl. No.: 727,883

[22] Filed: Oct. 9, 1996

Related U.S. Application Data

[63] Continuation of Ser. No. 246,814, May 20, 1994, Pat. No. 5,641,636.
[51] Int. Cl.$^6$ .................................................. G01N 33/53
[52] U.S. Cl. .......................... 435/74; 435/18; 435/23; 435/24; 436/518; 436/530; 436/531
[58] Field of Search .......................... 435/7.1, 7.4, 18, 435/23, 24; 436/518, 528, 529, 530, 531

[56] References Cited

U.S. PATENT DOCUMENTS

| | | |
|---|---|---|
| 4,235,885 | 11/1980 | Sundeen et al. |
| 4,263,293 | 4/1981 | Sundeen et al. |
| 4,276,284 | 6/1981 | Brown |
| 4,297,275 | 10/1981 | Sundeen et al. |
| 4,367,233 | 1/1983 | Clark et al. |
| 4,371,465 | 2/1983 | McGregor |
| 4,371,466 | 2/1983 | McGregor |
| 4,374,765 | 2/1983 | McGregor |
| 4,382,081 | 5/1983 | Sundeen et al. |
| 4,558,034 | 10/1985 | Galardy et al. |
| 4,704,383 | 11/1987 | McNamara et al. |
| 4,992,537 | 2/1991 | Goldberg |
| 5,096,830 | 3/1992 | Senyei et al. |

FOREIGN PATENT DOCUMENTS 9323075  11/1993  WIPO.

OTHER PUBLICATIONS

Vadillo–ortega et al, American Journal of Pathology, 146 (1):148 –156, 1995.
Lei et al, Biology of Reproduction, 53:339 –344, 1995.
Vadillo–Ortega et al, Am J. Obstet. Gynecol., 174: 1371 –1376, 1996.
So et al., Biol. Reprod. 46:772–8 (1992).
So et al., Acta Obst. Gynec. (Jpn) 45(3):227–233 (1993).
McCormick, N. Engl. J. Med. 312:82–90 (1985).
McCormick, M., "Trends in Rates of Low Birthweight in the United States,"In Berendes HW, Kessel S, Yaffe S. (eds.) Advances In The Prevention of Low Birthweight, Washington, D.C.: National Center for Education in Maternal and Child Health, 1991:3–11.
Rush et al., BMJ 2:965–8 (1976).
Creasy et al., Obstet. Gynecol. 76 Suppl:2S–4S (1990).
Creasy, N. Engl. J. Med. 325(10):727–8 (1991).
Main et al., Am. J. Obstet. Gynecol. 151:892–8 (1985).
MacLennan et al., Lancet 335:267–9 (1990).
Lockwood et al., N. Eng. J. Med. 325(10):669–74 (1991).
Matsuura et al., Proc. Natl. Acad. Sci. USA 82:6517–21 (1985).
Romero et al., Contemp. OB/GYN, May 1993, 33–44.
Skinner et al., Obstet. Gynecol. 57:487–9 (1981).
Al–Zaid et al., Br. J. Obstet. Gynecol. 87:227–9 (1980).
Evaldson et al., Gynecol. Obstet. Invest. 29:92–94 (1987).
Vadillo–Ortega, Obstet. Gynecol. 75:84–8 (1990).
Katsura et al., FEBS Letters 244(2):315–18 (1989).
Fernandez et al., Lab. Invest. 66:572–579 (1992).
Woessner, FASEB J. 5:2145–54 (1991).
Okada et al., J. Biol. Chem. 267(30):21712–19 (1992).
Barrett et al., Biochem. J. 133:709–724 (1973).
Hibbs et al., J. Biol. Chem. 260:2493–2500 (1985).
Moll et al., Cancer Res., 50:6162–70 (1990).
Morodomi et al., Bioche. J. 285:603–11 (1992).
Ramos–DeSimone et al., HYBRIDOMA 12(4):349–63 (1993).
Manicourt et al., Anal. Biochem. 215(2):171–9(1993)
Towbin et al., Proc. Natl. Acad. Sci. USA 76(9):4350–4354 (1979).
Boone et al., Proc. Natl. Acad. Sci. USA 87:2800–04 (1990).
DeClerk et al., J. Biol. Chem. 264:17445–53 (1989).
Bickett et al., Anal. Biochem. 212(1):58–64 (1993).
Landolphi, J. Immunol. 146(3):915–19 (1991).
Goldberg, J. Biol. Chem. 267(7):4583–4591 (1992).
"Home Monitors for High–Risk Pregnancies Get Critical Look,"in *Health Technology Trends*, Sep.1992, at pp. 3,5.
Malak et al., Br. J. Obstet. 101:375–86 (1994).
Vadillo–Ortega et al., Am J. Obstet. Gynecol., (Feb.1991) 164(2):664–668.
Huessen et al., Anal. Biochem. Biophys., (1980) 259:576–588.

*Primary Examiner*—Marianne P. Allen
*Assistant Examiner*—Patricia A. Duffy
*Attorney, Agent, or Firm*—Lerner, David, Littenberg,Krumholz & Mentlik

[57] ABSTRACT

Disclosed is a method of predicting the onset of fetal membrane rupture in a gestative female comprising the step of assaying a tissue or fluid sample of fetal membrane origin obtained from the female for the presence of pro-metalloproteinase-9 (pro-mmd-9). The presence of pro-mmd-9 in the sample is a positive indication of the onset of fetal membrane rupture. Also disclosed is a method of delaying the onset of female membrane rupture in a gestative female comprising the step of administering to the female an MMP-9 inhibitor in an amount effective to delay fetal membrane rupture. Further disclosed is a method of inducing labor in a gestative female comprising the administration of an MMP-9 activator or MMP-9 itself in an amount effective to induce fetal membrane rupture, and thus facilitate the onset of labor.

18 Claims, 3 Drawing Sheets

METHOD OF PREDICTING FETAL MEMBRANE RUPTURE BASED ON PRO-MATRIX METALLOPROTEINASE-9 (PRO-MMP-9)

This is a continuation of application Ser. No. 08/246,814 filed May 20, 1994, now U.S. Pat. No. 5,641,636.

FIELD OF THE INVENTION

The present invention relates to the field of obstetrics and gynecology, and particularly to the biochemistry surrounding the phenomenon of fetal membrane rupture.

BACKGROUND OF THE INVENTION

Premature or preterm delivery of otherwise normal babies is a problem throughout the world, in both developed and developing countries. In fact, delivery of infants before the completion of 37 weeks of gestation is the leading cause of neonatal morbidity and mortality in the United States, McCormick, N. Engl. J. Med. 312:82–90 (1985), where the incidence of such deliveries has hovered around 7–9% for many years. McCormack M., "Trends in Rates of Low Birthweight in the United States," In Berendes HW, Kessel S, Yaffe S, (eds.) Advances In The Prevention Of Low Birthweight, Washington, D.C.: National Center for Education in Maternal and Child Health, 1991:3–11. Studies have shown that preterm neonates account for more than half, and perhaps as much as 75%, of the mortality and morbidity among newborns without congenital abnormalities. Rush et al., BMJ 2:965–8 (1976). Although various intervention programs have claimed success in reducing the number of preterm deliveries, the results have been difficult to reproduce or sustain. See, e.g., Creasy et al., Obstet. Gynecol. 76:Suppl: 2S–4S (1990). Thus, as perinatal mortality and morbidity due to other causes have decreased, the relative magnitude of the problem of preterm delivery has grown, despite the significant improvement in neonatal care. Creasy, N. Engl. J. Med. 325(10):727–8 (1991).

The medical profession has acknowledged that preventing preterm labor or rupture of the membranes is far more desirable than dealing with the problem after the fact. Id. A solution to the problem has been exacerbated because preterm birth is a multifaceted problem with different causes. Most of the current approaches to the prevention of preterm birth rely in part on risk-scoring systems to identify a group of women to whom special attention can be directed. Id. These rely on such factors as obstetrical history, demographic factors, and premonitory symptoms. Main et al., Am. J. Obstet. Gynecol. 151:892–8 (1985). However, these approaches have been roundly criticized as being neither sensitive nor specific. Id. For example, application of these methods to multiple pregnancies, including bed rest in pregnancies with twins, has been shown to be of little value. MacLennan et al., Lancet 335:267–9 (1990). Current treatment regimens have also been frequently hampered by an advance stage of labor or the inability to distinguish between irrelevant contractions and true preterm labor. Lockwood et al., N. Engl. J. Med. 325(10):669–74 (1991). Thus, effective preventative measures have been essentially unavailable, largely because of the inability to predict the problem with enough certainty to warrant enrolling patient in a trial of preventative approaches. Creasy et al., supra.

A major focus of research has been to find a biochemical marker predictive of spontaneous preterm labor or premature rupture of the fetal membranes. Various candidates for biochemical markers of preterm delivery, e.g., plasma estradiol-17 beta, progesterone, and C-reactive protein, have not withstood rigorous scrutiny. Lockwood, supra. Lockwood et al. studied fetal fibronectin as a marker candidate, based upon the previous identification of this ubiquitous plasma and extracellular matrix protein in amniotic fluid and placental tissue. Matsuura et al., Proc. Natl. Acad. Sci. USA 82:6517–21 (1985). Lockwood's hypothesis was that mechanical or inflammatory-mediated damage to the fetal membrane before preterm delivery results in the release of fibronectin into the cervix and vagina. Lockwood was optimistic about the results; however, the group cautioned that further studies must be conducted to determine whether the presence of fibronectin in cervicovaginal secretions can not only identify asymptomatic patients at risk for term delivery, i.e., contractions are recognized, but also determine the time interval between a positive test and the beginning of preterm labor so that therapy could be initiated. Lockwood's conclusions were later criticized on the ground that the fetal-fibronectin test may have a clinically important false positive rate if used to diagnose ruptured membranes. Creasy et al., supra. Creasy cast further doubt in Lockwood's work by offering an alternative hypothesis for the presence of fetal fibronectin in cervicovaginal fluids which did not implicate fetal membranes.

The chorioamniotic membranes are essentially connective tissue structures. Since collagen determines the tensile strength of fibrous connective tissue, there has been considerable interest in investigating collagen biochemistry in the setting of premature fetal membrane rupture. See Romero et al., Contemp. OB/GYN, May 1993, 33–44. Some investigators have detected low collagen content in membranes that have ruptured prematurely as compared with normal membranes, and suggested that the tensile property of the amniotic membranes in the former cases must be lower than in normal membranes. See Skinner et al., Obstet. Gynecol. 57:487–9 (1981). However, other groups have found no difference in the connective tissue collagen content in prematurely ruptured fetal membranes. See Al-Zaid et al., Br. J. Obstet. Gynaecol. 87:227–9 (1980); Evaldson et al., Gynecol. Obstet. Invest. 29:92–4 (1987). There have been yet other reports of high levels of collagenolytic activity in prematurely ruptured fetal membranes and in the serum of women with preterm labor. See, e.g., Vadillo-Oretega, Obstet. Gynecol. 75:84–8 (1990). However, the precise mechanism for these biochemical changes has remained unknown. See Katsura et al., FEBS Letters 244 (2):315–18 (1989); So et al., Biol. Reprod. 46:772–8 (1992). Enzymes capable of degrading collagen have been previously described as products of cultured cells derived from fetal membranes. So et al., Acta. Obst. Gynaec. (Jpn) 45 (3):227–233 (1993).

The immunocytochemical detection of collagenase (MMP-2) in fetal membranes was reported in Fernandez et al., Lab. Invest. 66:572–579 (1992). The enzyme family known as matrix metalloproteinases (MMPs) has been implicated in many normal tissue remodeling processes such embryonic development, postpartum involution of the uterus, bone and growth plate remodeling, ovulation, and wound healing, as well as pathological conditions such as arthritis, tumor invasion and metastasis. See Woessner, FASEB J. 5:2145–54 (1991). While these enzymes may act on certain common substrates such as denatured collagen (gelatin) in vitro, they undoubtedly have specific natural substrates in vivo which account for their distinct roles in specific cellular processes. The enzymes described by So et al., namely MMP-1 and MMP-3, have not been correlated with structural changes in fetal membranes.

3

Hence, a need remains for a more specific and reliable biochemical marker with which to diagnose or predict fetal membrane rupture.

SUMMARY OF THE INVENTION

In having provided a solution to the problem confronted by those in the art, the present invention is directed to a method of predicting the onset of fetal membrane rupture in a gestative female containing the step of assaying a tissue or fluid sample of fetal membrane origin obtained from the female for the presence of metalloproteinase-9 activity. The presence of such activity in the sample is a positive indication of the onset of fetal membrane rupture.

In another embodiment of the present invention, a method of delaying the onset of fetal membrane rupture in a gestative female is provided. A gestative female is treated with an MMP-9 inhibitor in an amount effective to delay fetal membrane rupture.

In a further embodiment of the present invention, a method of inducing labor in a gestative female is provided. A gestative female is administered an MMP-9 activator or the MMP-9 enzyme itself in an amount effective to induce fetal membrane rupture, which in turn facilitates the onset of labor.

Applicants' invention is predicated upon their unexpected and surprising discovery that metalloproteinase-9 ("MMP-9"), and particularly its active species, are present in human fetal membranes, particularly the amnion epithelium, fibroblasts, and chorion laeve trophoblast cells, only during labor or after delivery. Specifically, active MMP-9 was detected in these tissue extracts from fetal membranes collected from women in active labor and after delivery. In contrast, however, substantially no MMP-9 activity was detected in membranes removed prior to the onset of labor. On the basis of these findings, and while not intending to be bound by any particular theory, Applicants hypothesize that activation of MMP-9 results in the degradation of collagenous matrix of the fetal membranes, and thus facilitates their rupture under both normal physiological and pathological conditions.

DETAILED DESCRIPTION OF THE PREFERRED EMBODIMENT

Figure 1:
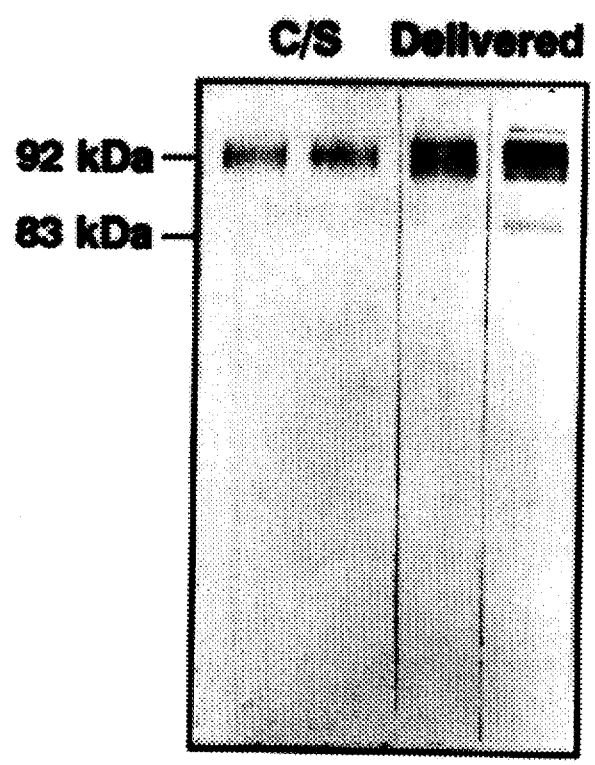
FIG. 1 is a Western blot analysis of MMP-9 protein in extracts of human amniochorion.

In a first embodiment according to the present invention, a tissue or fluid sample of fetal membrane origin obtained from a gestative female is assayed for the presence of MMP-9 activity, wherein the detection of such activity is a positive indication of the onset of fetal membrane rupture.

To enhance the reliability and accuracy of the method, the sample is necessarily of fetal membrane origin. The sample can be a tissue, e.g., a biopsy of the membrane, or a fluid which is either contiguous to the membrane or otherwise interactive with the membrane in such a way that its biochemical constituency particularly its MMP-9 concentration, is fairly representative of the state of the membrane at any given time during gestation. Examples of such fluids include cervicovaginal fluids, e.g., cervical fluid or vaginal fluid, plasma and serum. Cervical fluid is preferred. Fluid samples, which are preferred, may be conveniently obtained with a swab or any other suitable collection device. The thus-obtained fluid sample can then be placed in a predetermined volume of extraction medium, e.g., SDS-PAGE sample buffer, that serves to remove proteins from the collection device. This medium can then be used as the test material for the assay of MMP-9 activity. Alternatively, the assay can be performed directly on the sample while it remains on the device.

MMP-9, also known as the 92-kDa type IV collagenase/gelatinase or gelatinase B, is the largest member of the matrix metalloproteinase enzyme family. The purification of MMP-9 and the cDNA sequence encoding the enzyme are disclosed in U.S. Pat. No. 4,992,537 (Goldberg et al.). The zymogen form of MMP-9, i.e., proMMP-9, is initially activated to produce an intermediate active form of about $M_r$ 83,000 Da (83 kDa) and a 9 kDa inactive proteolytic cleavage fragment, which is then further proteolytically processed to yield an active species of about $M_r$ 67,000 Da (67 kDa) and a 16 kDa inactive proteolytic cleavage product. See, for example, Okada et al., J. Biol. Chem. 267(30):21712–19 (1992). All active species have the ability to bind to $alpha_2$ macroglobulin. Barrett et al., Biochem. J. 133:709–724 (1973). Thus, by the term "MMP-9 activity," it is meant the presence of any active, e.g., gelatinolytic, species of MMP-9 such as the intermediate 83 kDa species and the 67 kDa species, which are the two most prominent catalytically active species of MMP-9, or their respective 9 and 16 kDa proteolytic cleavage products. See Okada et al., Woessner, supra.

MMP-9 activity can be performed in accordance with a variety of art-recognized procedures. For example, quantitative zymographic methods provide a relatively refined assessment of the activity of this enzyme. This method allows for the detection of MMP-9 activity based upon the ability of the enzyme to hydrolyze denatured collagen, i.e., gelatin, which is a natural substrate for MMP-9. The gelatin is incorporated into a gel such as polyacrylamide. See Hibbs et al., J. Biol. Chem. 260:2493–2500 (1985) and Moll et al., Cancer Res. 50:6162–70 (1990). The assay may be standardized using a purified MMP-9 preparation that is analyzed in parallel with the test sample. Purified MMP-9 can be prepared by methods known in the art. See, for example, Okada et al., supra., and Morodomi et al., Biochem J. 285:603:11 (1992). The extent of hydrolysis of the gelatin is directly related to the activity of MMP-9 in the sample, and the active MMP-9 forms can be identified by their characteristic molecular weights. In the gelatin zymography, the proMMP-9 species can be detected because of the catalytic activation that occurs during electrophoresis and subsequent incubation. However, the MMP-9 forms present prior to the onset of labor are incapable of undergoing this kind of activation, i.e., they are latent.

MMP-9 activity can also be detected using standard immunological techniques, e.g., ELISA, immunofluorescence assays, or radioimmunoassays. In a preferred embodiment, MMP-9 activity is detected using ELISA, which entails the use of antibodies specific to MMP-9. See David et al., U.S. Pat. No. 4,376,110 (and references cited therein). Monoclonal antibodies specific to MMP-9 have been prepared using partially purified enzyme preparations. See, e.g., Moll et al., supra; Ramos-DeSimone et al., HYBRIDOMA 12(4):349–63 (1993) and Goldberg et al. Polyclonal antibodies specific to MMP-9 can also be prepared in accordance with standard procedures. In a preferred embodiment, polyclonal antibodies are prepared using non-conserved peptides conjugated to a macromolecular carrier. The choice of a specific non-conserved peptide such as the metal-binding domain, among the members of the MMPs is considered within a level of ordinary skill in the art. See Woessner, and Goldberg et al., supra. Enzymic assays that can detect MMP-9 in picogram or nanogram amounts are also disclosed in Manicourt et al., Anal. Biochem. 215(2):171–9 (1993).

MMP-9 activity can further be detected in a sample by western blot analysis, which requires electrophoretic separation of the test material in a gel, followed by transfer of the separated proteins to a nitrocellulose membrane and detection of the MMP-9 antigens with a specific antibody and reagent that reacts with the antigen-fixed antibody. See Towbin et al., Proc. Natl. Acad. Sci. USA 76(9):4350–4354 (1979).

In the cases where MMP-9 activity is measured by the presence of the inactive proteolytic cleavage products, such detection must be performed immunologically using antibodies specific to these products.

As mentioned above, an MMP-9 detection reagent may be fixed to the collection device, whereupon the detection of MMP-9 activity that is accomplished by exposing the collection device to a detectably labeled reagent specific to the enzyme, followed by development of a visual signal, e.g., an enzyme-based color reagent, which indicates the presence of active MMP-9. This assay methodology is currently employed in urinary pregnancy tests and ovulation prediction tests.

While the detection of the presence of MMP-9 activity in many cases can be taken as a positive indication of the onset of fetal membrane rupture, the reliability of the method can be enhanced by quantifying the MMP-9 activity in the given sample and then comparing it to an established control level of MMP-9 activity (e.g., prepared by a prospective longitudinal analysis of normal specimens collected from women who delivered at term). One skilled in the art would necessarily expect that this threshold value would be substantially negligible in view of Applicants' finding that MMP-9 exists in a latent form prior to labor. That is, any non-negligible MMP-9 activity should be taken as predictive of the onset of labor. Since labor may occur within a matter of days or even hours, close monitoring of the patient should be initiated immediately. Samples should be obtained from the patient periodically thereafter, e.g., daily or even more frequently, to generate a time course analysis of the expression of active MMP-9 such that effective therapeutic intervention can be employed.

In view of the working hypothesis that the underlying biochemical mechanisms surrounding fetal membrane rupture are substantially identical in both normal and pathological conditions, the method of the present invention is equally predictive of the onset of term labor as well as pre-term labor. By "term labor," it is meant labor which occurs at the end of a normal gestation, i.e., at about week 37. See Romero et al., Lockwood et al., supra. The term "pre-term labor" refers to the onset of labor any time therebefore, and "post-term" labor refers to the onset of labor thereafter. Thus, the method of the present invention is advantageously practiced to identify patients at risk of premature membrane rupture, as well as to monitor patients already suspected of being at risk, e.g., those characterized by structural abnormalities, predisposition to fetal membrane rupture, prior delivery of twins, or a history of drug or alcohol abuse, diabetes or hypertension. In these cases, the present invention can be employed beginning during the second trimester of pregnancy, e.g., at about the 22nd or 23rd week, and periodically (e.g., daily, weekly, or more or less frequently) thereafter depending on such factors as the results of the previous assay. The method is further effectively practiced on ostensibly low risk patients to further investigate any sudden cervical changes, or simply as a routine measure during the last trimester of pregnancy to provide a more accurate prediction of the delivery date.

In another embodiment of the present invention, an MMP-9 inhibitor is administered to a gestative female, particularly one suspected of an imminent risk of fetal membrane rupture, to delay such membrane rupture. By the term "MMP-9 inhibitor," it is meant any natural or synthetic substance capable of rendering active MMP-9 species catalytically inactive, rendering proMMP-9 incapable of being proteolytically processed to its active forms, or rendering endogenous activators of MMP-9 inactive.

Several inhibitors of MMP-9 are known in the art. These include, for example, a 29 kDa tissue inhibitor of metalloproteinase-1 ("TIMP-1") (Moll et al., supra.), 1, 10-phenanthroline, and monoclonal antibodies specific to MMP-9 (Ramos-DeSimone, supra.). The cDNA sequence of TIMP-1 is disclosed in Boone et al., Proc. Natl. Acad. Sci. USA 87:2800–04 (1990). The purification of TIMP-1 is disclosed in DeClerk et al., J. Biol. Chem. 264:17445–53 (1989). Various chelating agents, e.g., EDTA (ethylene diamine tetraacetic acid) bis-(dioxopiperazine)s, particularly 2,6-dioxopiperazines also have been found to inhibit type IV collagenases in vivo. See W.O. 9323075 (PCT/US93/04542) (Liang et al.), and the references cited therein, including the collagenase inhibitors disclosed in U.S. Pat. Nos. 4,367,233; 4,371,465; 4,371,466; 4,374,765; 4,235,885; 4,263,293; 4,297,275; 4,382,081; 4,558,034; 4,276,284; and 4,704,383. Other inhibitors of MMP-9 would include enzymes such as proteases which provide for the inactivation of MMP-9 by cleaving it into inactive fragments, and antisense RNAs. Those skilled in the art could determine other therapeutically effective inhibitors of MMP-9 in accordance with standard screening assays. See Bickett et al., Anal. Biochem. 212(1):58–64 (1993), and Liang et al. The inhibitor TIMP-1, for example, could be modified (to produce an analog conjugate or derivative) to increase both potency and half-life such as by preparing a complex of this inhibitor with an IgG molecule having a disarmed effector function. See Landolphi, J. Immunol. 146(3):915–19 (1991).

The MMP-9 inhibitors are administered in an amount effective to delay fetal membrane rupture, which in turn would delay the onset of labor. From a clinical point of view, it would be especially advantageous to delay the onset of labor until at least 30 weeks, and preferably 34 weeks of gestation. This time would allow the fetus to mature, and thus increase the chances of survival. The dosage amount and mode of administration of any given inhibitor would depend on several factors including the chemical nature of the inhibitor and the seriousness of the condition. In general, an effective amount of the inhibitor which is administered to the patient will range from at least 0.1 mg/kg of body weight per day to about 100 mg/kg of body weight per day. Those skilled in the art would be able to determine preferred dosage amounts using suitable experimental models such as subhuman primates (e.g., baboon).

The MMP-9 inhibitors may be administered by any pharmaceutically acceptable means, e.g., orally, parenterally. Intra-amniotic or parenteral delivery and vaginal suppositories are preferred. Of course, those skilled in the art appreciate that the rate of the administration of the MMP-9 inhibitor can be achieved by the use of sustained-release drug delivery systems known in the art. However, those skilled in the art would appreciate that other modes of administration could be effectively used.

In a further embodiment of the present invention, MMP-9, e.g., substantially purified MMP-9, or an MMP-9 activator is administered to a gestative female to induce fetal membrane rupture which in turn facilitates the onset of labor. By the term "MMP-9 activator," it is meant any pharmaceutically acceptable natural or synthetic substance that reacts with endogenous proMMP-9 to produce an active MMP-9 species, or which activates or otherwise stimulates expression of an endogenous activator of MMP-9. A variety of MMP-9 activators such as chemical agents, cytokines, growth factors, prostanoids (e.g., prostaglandin $E_2$), repressive factors, as well as other sundry agents are known in the art. See Woessner, supra. A preferred chemical agent is 4-aminophenylmercuric acetate (APMA). Other preferred activators include the cytokines such as interleukin-1 alpha and tumor necrosis factor alpha. See So et al, Biol. Reprod. 46:772–8 (1992), Okada et al., and Liang et al., supra. Trypsin has also been disclosed as an effective activator of proMMP-9. See Morodomi, supra.

MMP-9 or an MMP-9 activator is advantageously administered to post-term patients (i.e., those for whom gestation is prolonged beyond 37 weeks), or otherwise when the patient or fetus is at risk. Alternatively, the method can be practiced as a matter of mere convenience provided, of course, that the fetus is fully mature. As in the case for the MMP-9 inhibitors, the determination of general and preferred dosage amounts, and the mode and frequency of administration of the MMP-9 activator or MMP-9 are considered within the level of skill in the art. Those teachings apply equally here. Further, those skilled in the art would appreciate that MMP-9 activators or MMP-9 can be delivered to achieve a sustained release effect or with increased half-life in accordance with the standard techniques described above.

The invention will be further described by reference to the following detailed examples. These examples are provided for purposes of illustration only, and are not intended to be limiting unless otherwise specified.

EXAMPLES

Fetal membranes were collected at term after normal delivery or at the time of elective cesarean section at term without labor. Whole membrane or amnion and chorion, manually separated, were processed for gelatin zymography and Western blot analyses as described below in Examples 1 and 2.

Example 1

Western Blot Analysis of MMP-9 in Human Term Fetal Membrane

Western blotting was carried out using 10 μg of protein per lane in 8% SDS-PAGE under non-reducing conditions. Transfer of protein to a Imunobilon-P membrane was carried-out using 30 V for 12 h at 4° C. using methods described by Towbin et al., supra. The monoclonal antibody 6-6B is disclosed in Ramos-DeSimone, supra. This antibody recognizes under non-reduced conditions both the proMMP-9 (92 kDa) and the intermediate active form of the enzyme (83 kDa). Primary antibody was used at 1 μg/ml and incubated with the blot overnight at 4° C. The primary antibody was detected with the VectaStain ABC reagents (Vector Laboratories, Burlingame, CA).

Western blot analyses revealed that MMP-9 was present in the amniochorion extracts from delivered fetal membranes as a broad band of 92–94 kDa (FIG. 1). A 83 kDa band representing the intermediate form of MMP-9 activation was seen only in specimens collected following delivery.

Example 2

Gelatin Zymographic Analysis of MMP-9 in Human Term Fetal Membranes Amnion and Chorion SDS-PAGE was performed according to Laemmli using a mini-gel apparatus (Bio-Rad, Richmond, CA). Gels were prepared according to the standard technique except that pig skin gelatin (1 mg/ml) was copolymerized in the 8% running gel and samples were added under non-denaturating conditions. Ten μg of protein were applied per lane and run under constant current (10 mA). Gels were washed in 2.5% Triton X-100 during 30 min and then incubated for 24 hr at 37° C. in 50 mM Tris buffer, pH 7.4, containing 0.15M NaCl and 30 mM $CaCl_2$ or a buffered solution to which 10 mM EDTA was added to inhibit MMP activity. Gels were stained with Coomasie R-250. Pre-stained molecular weight markers (Bio-Rad) were included in each gel.

Figure 2A:
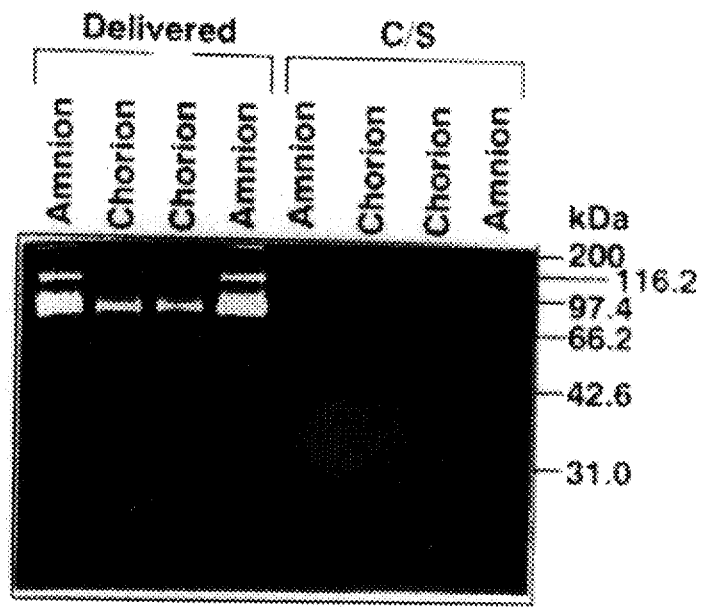
FIGS. 2A and B are gelatin zymographic analyses of extracts of human amnion and chorion manually separated from fetal membranes collected at cesarean section (C/S) or following delivery ("Delivered"), in the absence (A) or presence (B) of 10 mM EDTA.
Figure 2B:
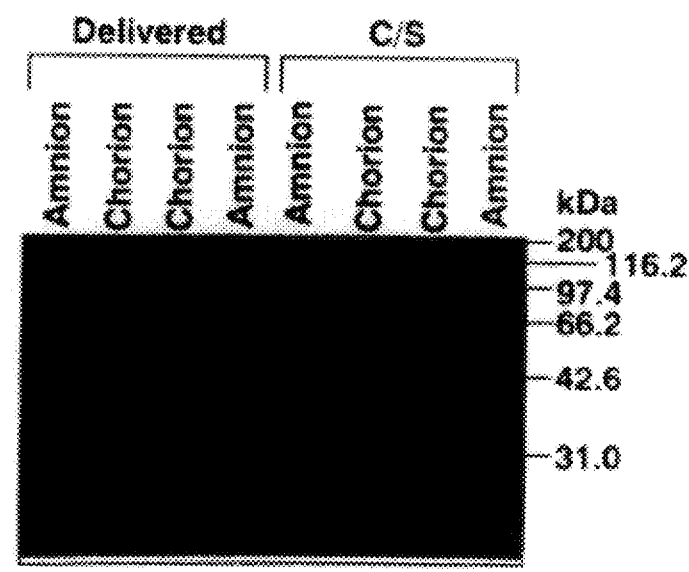

Extracts of amniochorion obtained following active labor produced five lysis bands in zymograms ranging in size from about 68 to 150 kDa with the most prominent band being a 92 kDa gelatinase. These activities were also present in separated amnion and chorion laeve, with greater activity consistently being found in amnion (FIG. 2A). Lytic activity in the amnion and chorion laeve extracts was completely inhibited in the presence of 10 mM EDTA, indicating that the gelatinases are MMPs (FIG. 2B). The molecular weights of the gelatinases suggest that MMP-9 is a primary component. Gelatin zymography can detect MMP-9 dimers (150 kDa), the 92 kDa proenzyme and activated enzyme species having molecular weights of 83 kDa and 68 kDa.

In marked contrast to the delivered membranes, extracts of amniochorion, and separated amnion and chorion laeve from women not in labor (elective cesarean section) had negligible gelatinase activity (FIG. 2A).

Example 3

Figure 3A:
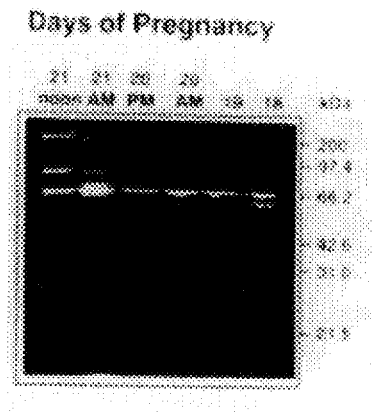
FIGS. 3A and B are polyacrylamide gel electrophoretic (PAGE) analyses of homogenized fetal membranes obtained from pregnant Sprague-Dawley rats killed at the indicated times during normal gestation.
Figure 3B:
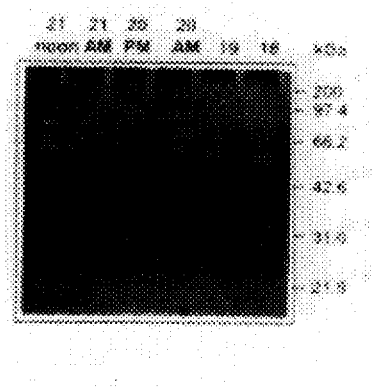
FIG. 3C is a 1% casein zymographic analysis of homogenized fetal membranes obtained from pregnant Sprague-Dawley rats killed at the indicated times during normal gestation.
Figure 3C:
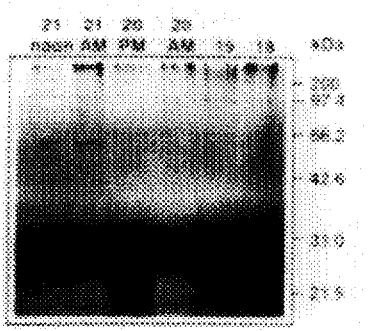

Demonstration of Correlation between MMP-9 Activity and Fetal Membrane Rupture in Rats Experiments were carried out to determine the extent of MMP-9 activity in pregnant rats. Amnions were collected from pregnant Sprague Dawley rats killed at days 18, 19, 20 (A.M.), 20 (P.M.), 21 (A.M.) and 21 (noon) during normal gestation. Delivery normally occurs on the late afternoon of day 21. The membranes were homogenized and equal amounts of protein (16 μg/lane) were subjected to polyacrylamide electrophoresis in gels impregnated with 1% gelatin (FIG. 3A and B) or 1% casein (FIG. 3C) for zymography. MMP-2, detected as a lysis zone around 68 kDa, was present in amnions collected on days. 18–21 (FIG. 3A). In contrast, MMP-9, detected as both a 92 kDa lysis zone and a dimer at 180 kDa, was present only on day 21 (FIG. 3A). Both MMP-2 and MMP-9 activities were not detected in the gels incubated in the presence of 10 mM EDTA (FIG. 3B). Caseinolytic activity, characteristic of MMP-9, was also detected only on day 21 at a molecular weight of 92 kDa (FIG. 3C). In conjunction with the appearance of MMP-9 activity beginning at about day 21, structural changes became apparent in the amnion at both the light and electron microscope level. These changes include a loss of collagen (observed as fibrils at the electron microscopic level) and proteoglycans and necrosis of amnion epithelial cells (as disclosed by ultrastructural analysis). These changes (observed by staining with Alcian blue and Periodic-Acid Schiff stain) resulted in alterations in the consistency of the amnion such that it became a fragile and viscous liquid-like.

These observations demonstrate that MMP-9 activity is detectable in amnion only from about 12 to about 18 hours before delivery. MMP-2 activity, on the other hand, appears to be constitutively expressed in the tissue. MMP-3 activity was not detectable in either gelatinolytic or caseinolytic assays. Since amnion structure changes dramatically on day 21 as determined by loss of collagen fibrils and proteoglycans detected by light and electron microscopy, these observations suggest that MMP-9 is responsible for the changes in amnion structure that precede membrane rupture.

MMP-1 and MMP-3 had previously been identified in cultured cells derived from fetal membranes. However, the data illustrated in FIGS. 3A–C clearly indicate that these two matrix metalloproteinases are not correlated with structural changes in fetal membranes in the rat model. Nor were these enzymes detected in getalinolytic or caseinolytic assays in human female membranes in association with labor. On the basis of these data, there appears to be no direct correlation between the presence of other known MMPs and the process of fetal membrane rupture.

Example 4

Quantitative Gelatin Zymography

A collection swab is placed into a 1.5 ml conical tipped tube containing 500 µl of SDA-PAGE sample buffer as disclosed in Laemmli, Nature 227:680–684 (1970). After 5 min at room temperature, the swab is withdrawn and the eluted proteins (in 30 µl of sample buffer) from the swab are subjected to SDS-PAGE, performed according to Laemmli using a mini-gel apparatus (Bio-Rad, Richmond, CA). Gels are prepared according to standard techniques except that pig skin gelatin (1 mg/mL) is copolymerized in the 8% running gel and samples are added under non-denaturating conditions. A series of standards consisting of purified human MMP-9, prepared as described by Okada et al, supra., and molecular weight markers are also run on the gel. The samples are electrophoresed under constant current (10 mA). Gels are then washed in 2.5% Triton X-100 during 30 min and then incubated for 24 h at 37° C. in 50 mM Tris Buffer, pH 7.4, containing 0.15M NaCl and 30 mM CaCl$_2$. Gels are stained with Coomasie R-250 and zones of lysis of the gelatin are visualized following destaining of the gels. The gels are analyzed with a Resource Technology (Nashville, Tenn.) image analyzer to determine the extent of gelatin lysis. A standard curve is constructed from the lysis zones of the pure MMP-9 standards.

Example 5

Western Blot Analysis of MMP-9

Samples are prepared for SDS-PAGE as described above. The samples (30 µl), purified MMP-9 standards and molecular weight markers are applied to 8% polyacrylamide gels and electrophoresed under nonreducing conditions as described above. After electrophoresis, the separated proteins are transferred to a nitrocellulose membrane using 30 V for 12 h at 4° C. as described by Towbin et al., supra. A monoclonal antibody, 6-6B, directed against MMP-9 (Ramos-DeSimone, et al.) that recognizes under nonreduced conditions both the pro-MMP-9 (92 kDa) and the active form of the enzyme (83 kDa) is incubated with the membrane at a concentration of 1 µg/ml overnight at 4° C. The primary antibody is detected with the Amersham ECL reagent system. The resulting X-ray film is analyzed densitometrically to quantitate MMP-9 forms in the sample using a standard curve generated with the MMP-9 standards.

Example 6

Sandwich Immunoassay of MMP-9

The collection swab is placed into a 1.5 ml conical tipped tube containing 500 µl of phosphate buffered saline containing 1% bovine serum albumin and 0.1% Triton X-100 to elute proteins. The immunoassay is carried out on microtiter plates coated with an affinity-purified polyclonal antibody raised against a synthetic peptide representing the non-conserved metal binding domain of MMP-9. Aliquots of the sample and a standard curve of purified MMP-9 are applied to the plates. The plates are then incubated for 1 hr at 37° C. The plates are then washed with phosphate buffered saline-1% albumin 0.1% Triton X-100. 6-6B monoclonal antibody, radiolabeled with $^{125}$I with the Bolton-Hunter reagent (10, 000 cpm, 1 µg/ml) is then added in a 200 µl volume and the plates are incubated for 1 hr at room temperature. The unbound radiolabeled 6-6B antibody is washed from the wells with the phosphate buffered saline (1% bovine serum albumin-0.1% Triton X-100) (three washes of 500 µl each). The radioactivity bound to the microtiter plates is then determined with a gamma counter. A standard curve is constructed by subtracting a blank value (wells to which no sample or standard were added) from those of the standard curve. The amount of MMP-9 in the samples is determined by interpolation from the standard curve.

All publications and patent applications mentioned in this specification are indicative of the level of skill of those skilled in the art to which this invention pertains. All these publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appended claims.

We claim:

1. A method of predicting the onset of fetal membrane rupture in a gestative female, comprising the steps of:
   (a) obtaining a tissue or fluid sample of fetal membrane origin from the female; and
   (b) detecting the presence or mount of pro-malrix metalloproteinase-9 (pro-MMP-9) in said sample, wherein the presence of pro-MMP-9, or an increase in the amount of pro-MMP-9 relative to a control amount of pro-MMP-9, is a positive indication of the onset of fetal membrane rupture in said female.

2. The method of claim 1, wherein said sample is obtained from the female prior to term.

3. The method of claim 1, wherein said sample is a fluid sample.

4. The method of claim 3, wherein said fluid sample comprises cervical fluid.

5. The method of claim 1, wherein said pro-MMP-9 is detected immunologically.

6. The method of claim 1, wherein said pro-MMP-9 is detected via quantitative zymography.

7. The method of claim 1, wherein said pro-MMP9 is detected via western blot analysis.

8. The method of claim 1, wherein said step of detecting pro-MMP-9 comprises measuring the amount of pro-MMP-9 in said sample, and comparing the thus-measured amount to the control amount of pro-MMP-9.

9. The method of claim 7, wherein said control level of pro-MMP-9 is obtained by measuring the amount of pro-MMP-9 periodically beginning at about the second trimester of pregnancy.

10. A method of predicting the onset of labor in a gestative female, comprising the steps of:
   (a) obtaining a tissue or fluid sample of fetal membrane origin from the female; and
   (b) detecting the presence or amount of pro-matrix metalloproteinase-9 (pro-MMP-9) in said sample, wherein the presence or increase in the amount of pro-MMP-9 relative to a control amount of pro-MMP-9, is a positive indication of the onset of labor in said female.

11. The method of claim 10, wherein said sample is obtained from the female prior to term.

12. The method of claim 10, wherein said sample is a fluid sample.

13. The method of claim 12, wherein said fluid sample comprises cervical fluid.

14. The method of claim 10, wherein said pro-MMP-9 is detected immunologically.

15. The method of claim 10, wherein said pro-MMP-9 is detected via quantitative zymography.

16. The method of claim 10, wherein said pro-MMP-9 is detected via western blot analysis.

17. The method of claim 10, wherein said step of detecting pro-MMP-9 comprises measuring the amount of pro-MMP-9, and comparing the thus-measured amount of pro-MMP-9 to the control amount of pro-MMP-9.

18. The method of claim 14, wherein the control amount or pro-MMP-9 is obtained by measuring the amount of pro-MMP-9 periodically beginning at about the second trimester of pregnancy.

* * * * *